(12) United States Patent
Boutin

(10) Patent No.: US 11,443,841 B2
(45) Date of Patent: Sep. 13, 2022

(54) SYSTEM FOR ASSISTING THE PREPARATION OF MEDICATION DOSE PACKS AND METHODS

(71) Applicant: SYNERGY MEDICAL BRG INC., Longueuil (CA)

(72) Inventor: Jean Boutin, Longeuil (CA)

(73) Assignee: Synergy Medical BRG Inc., Longueuil (CA)

( * ) Notice: Subject to any disclaimer, the term of this patent is extended or adjusted under 35 U.S.C. 154(b) by 0 days.

(21) Appl. No.: 15/115,383

(22) PCT Filed: Feb. 3, 2015

(86) PCT No.: PCT/CA2015/050077
§ 371 (c)(1),
(2) Date: Jul. 29, 2016

(87) PCT Pub. No.: WO2015/113167
PCT Pub. Date: Aug. 6, 2015

(65) Prior Publication Data
US 2017/0177831 A1 Jun. 22, 2017

Related U.S. Application Data

(60) Provisional application No. 61/935,053, filed on Feb. 3, 2014.

(51) Int. Cl.
*G16H 20/13* (2018.01)
*G07F 17/00* (2006.01)
*A61J 1/03* (2006.01)

(52) U.S. Cl.
CPC .............. *G16H 20/13* (2018.01); *A61J 1/035* (2013.01); *G07F 17/0092* (2013.01)

(58) Field of Classification Search
CPC .... G07F 17/0092; G06F 19/3462; A61J 7/04; A61J 7/0069
See application file for complete search history.

(56) References Cited

U.S. PATENT DOCUMENTS 7,848,846 B2 12/2010 Uema et al.
2009/0152291 A1 6/2009 Ohmura et al.
(Continued)

OTHER PUBLICATIONS

"Office Action corresponding to Canadian Application No. 2,938,321 dated Dec. 23, 2021".

*Primary Examiner* — Timothy R Waggoner
(74) *Attorney, Agent, or Firm* — Myers Bigel, P.A.

(57) ABSTRACT

A system for assisting a manual filling of at least two dose packs laid on a support surface wherein each said dose pack has receptacles adapted to receive medication items based on dose pack prescription profiles. The system generally has a dose pack medication localizer for determining a location of each receptacle of each said dose pack, and for identifying medication items required in each said receptacle using the dose pack prescription profiles; a medication grouper for grouping, for each of the medication items of the dose pack prescription profiles of all of the dose packs, the locations of each said receptacle to be filled with a corresponding one of the medication items; a distribution matrix generator for generating a distribution sequence for filling the dose packs using each one of said grouping; and an output for producing a visual representation of the distribution sequence.

22 Claims, 2 Drawing Sheets

(56) References Cited

U.S. PATENT DOCUMENTS

| | | |
|---|---|---|
| 2009/0210247 A1 | 8/2009 | Chudy et al. |
| 2010/0121486 A1* | 5/2010 | Yuyama .................. G07F 11/44 700/227 |
| 2013/0018503 A1 | 1/2013 | Carson et al. |
| 2013/0026174 A1 | 1/2013 | Yuyama et al. |
| 2013/0218330 A1* | 8/2013 | Chudy ................ G06F 19/3462 700/244 |
| 2014/0261883 A1 | 9/2014 | Dent et al. |

* cited by examiner

SYSTEM FOR ASSISTING THE PREPARATION OF MEDICATION DOSE PACKS AND METHODS

CROSS-REFERENCE TO RELATED APPLICATION

The present application claims priority of provisional U.S. Provisional Patent Application Ser. No. 61/935,053, filed on Feb. 3, 2014, incorporated herein by reference.

FIELD OF THE APPLICATION

The present application relates to clients-specific medication packaging such as dose packs, multi-dose blister cards and the like for clients taking a plurality of different medication items in tablet or capsule form and, more particularly, to a system and method for assisting in the preparation of client-specific medication packaging.

BACKGROUND OF THE ART

Doses of medication over given periods vary as a function of the type of medication and the condition of the client, i.e., the prescription of the client. Clients are often required to take a plurality of doses over different periods of a day, and this often leads to confusion. It may be difficult for a client to respect the prescription details (e.g., intake time, quantity) when the doses and the types of medication are numerous.

One well known method used by pharmacists to overcome this problem is to provide the client with a client-specific dose pack having an array of receptacles, with each receptacle corresponding to a particular time of a day at which medication is to be taken. Such dose packs typically contain four or less/more receptacles per day for seven days, and these receptacles are in the form of sealed cups filled with appropriate medication by pharmacists as a function of the prescription, as determined by physicians' prescription. Other configurations exist, such as monthly dose cards, featuring between 28 and 31 receptacles, with one such dose card per day, or one such dose cards for morning medication, another for lunch medication, and so forth. Some dose cards even have 32 receptacles which enables the use of the additional receptacle(s) for extra pills in cases of loss, for instance. These dose packs may be known and referred to as multi-dose blister cards, as each receptacle is sealed by a blister for safety purposes.

The process of preparing these dose packs is labor-intensive, in that each receptacle must be filled individually by hand. Therefore, although the dose pack facilitates the intake of medication by clients, a substantial amount of time is required to fill these packs. Robotic systems have thus been devised to perform some of the filling operations. Robotic systems may however represent an important capital expense.

SUMMARY OF THE APPLICATION

It is therefore an aim of the present disclosure to provide a system and method for assisting the preparation of medication dose packs that addresses issues related to the prior art.

Therefore, in accordance with the present application, there is provided a system for assisting a manual filling of at least two medication dose packs laid on a support surface, each said medication dose pack having receptacles adapted to receive medication items based on dose pack prescription profiles, the system comprising: an assistance processor comprising: a dose pack medication localizer for determining a location of each receptacle of each said medication dose pack on the support surface, and for identifying medication items required in each said receptacle of each said dose packs using the dose pack prescription profiles; a medication grouper for grouping, for each of the medication items of the dose pack prescription profiles of all of the at least two medication dose packs, the locations of each said receptacle of each said dose packs on the support surface to be filled with a corresponding one of the medication items; and a distribution matrix generator for generating a distribution sequence for filling the dose packs on the support surface using each one of said grouping; and an output for producing a visual representation of the distribution sequence for assisting the manual filling of the dose packs with the medication items.

Further in accordance with the present application, the assistance processor is configured to receive position data for each said dose pack from an input for said determining the locations of the receptacles of the dose packs on the support surface.

Still further in accordance with the present application, the dose pack medication localizer is configured to determine the locations of the receptacles of each dose pack based on positions of each dose pack on the support surface and on a standard configuration of the dose pack.

Still further in accordance with the present application, the system includes a safety module for authenticating an operator operating the assistance processor.

Still further in accordance with the present application, the output is adapted to provide the visual representation on the support surface, over said dose packs, and indicate which receptacles are to be filled for each one of said grouping.

Still further in accordance with the present application, the assistance processor further comprises a filling verifier for verifying that the right medication item is used for the filling of the receptacles associated with each one of said grouping.

Still further in accordance with the present application, the filling verifier is configured to cause the output to display a visual validation grid for verifying dose packs after filling in accordance with the distribution sequence.

Still further in accordance with the present application, the distribution matrix generator is configured to keep track of the filling of the medication dose packs based on an inventory of the medication items for each grouping.

Still further in accordance with the present application, the distribution matrix generator is configured to identify the filling of one of the dose packs as incomplete based on said tracking.

In accordance with the present application, there is provided a method for assisting an operator for filling of at least two medication dose packs laid on a support surface, the method comprising: obtaining dose pack prescription profiles for each of the at least two medication dose packs; determining locations of receptacles of the medication dose packs on the support surface; grouping, for each one of a plurality of medication items of the dose pack prescription profiles of all of the at least two medication dose packs, the locations of each receptacle of each said medication dose packs to be filled with a corresponding one of the plurality of medication items; and generating and outputting a distribution sequence having steps each indicating which receptacles of the medication dose packs to fill in accordance with one of said grouping and to be performed sequentially for filling the medication dose packs.

Further in accordance with the present application, the method further comprises, for each one of the steps of the distribution sequence, verifying that the medication item used by the operator corresponds to that of the step of the distribution sequence.

Still further in accordance with the present application, said verifying includes tracking the filling of the medication dose packs based on an inventory of the medication items for each grouping.

Still further in accordance with the present application, said tracking includes identifying one of the medication dose packs as incomplete based on said tracking.

Still further in accordance with the present application, the method further comprises outputting an identity label for the filled one(s) of the medication dose packs based on said tracking.

Still further in accordance with the present application, the method further comprises sequentially outputting a visual representation of the steps of the distribution sequence for assisting the manual filling of the medication dose packs with the medication items.

Still further in accordance with the present application, the method further comprises verifying that the receptacles associated with one of the steps are filled with the corresponding medication item prior to outputting a subsequent step of the distribution sequence.

Still further in accordance with the present application, said outputting includes providing the visual representation on the support surface, over said medication dose packs, and indicating which receptacles are to be filled for each one of said grouping.

Still further in accordance with the present application, said determining includes receiving data from an input operable by an operator.

Still further in accordance with the present application, the method further comprises outputting a visual validation grid for verifying the dose packs after filling in accordance with the distribution sequence.

DESCRIPTION OF THE PREFERRED EMBODIMENTS

Figure 1:
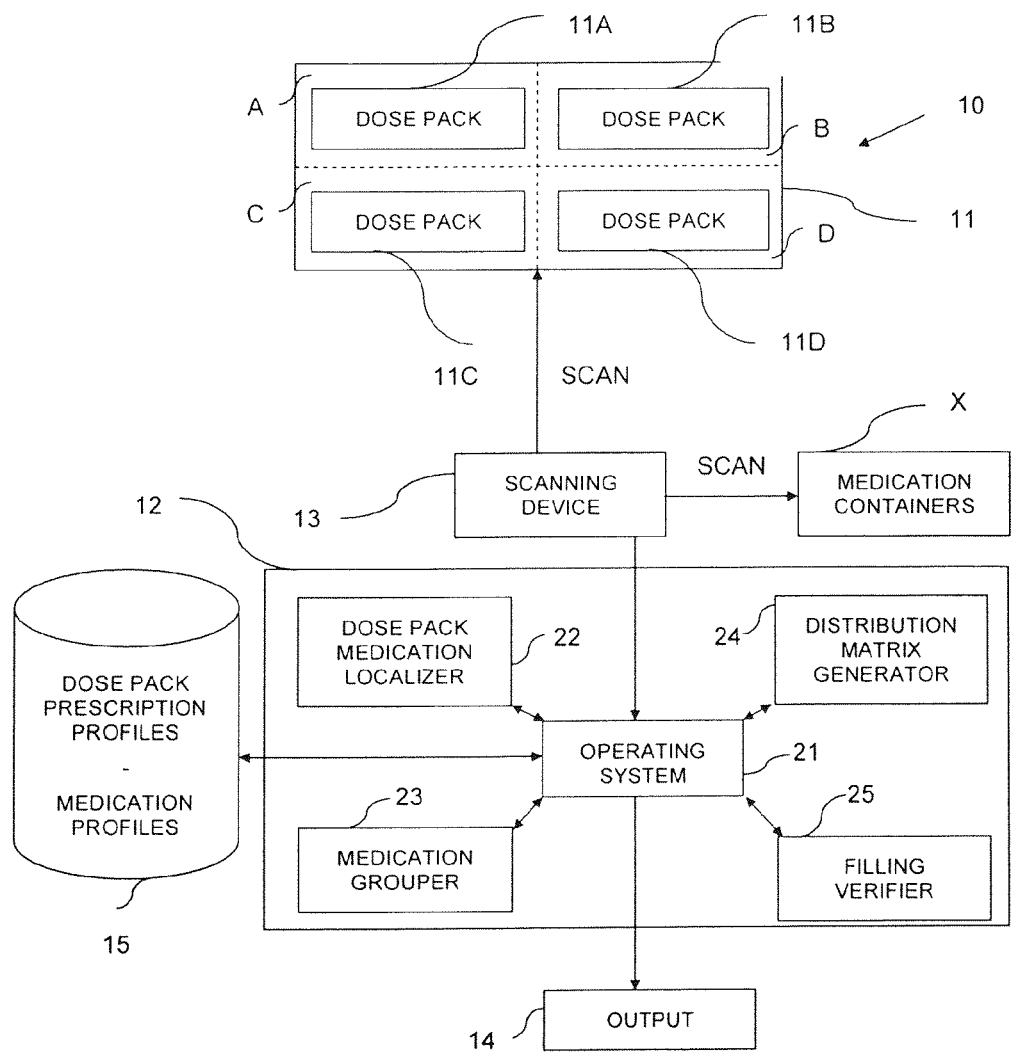
FIG. 1 is a block diagram of a system for assisting the preparation of medication dose packs in accordance with the present disclosure.

Referring to the drawings and more particularly to FIG. 1, there is generally illustrated at 10 a system for assisting the manual preparation of client-specific medication dose packs, in accordance with the present disclosure. For simplicity purposes, reference is made herein to dose pack of medication, although numerous other names could be used, such as multi-dose blister cards, client-specific medication cards or trays, for example. The dose packs typically consist of an array of receptacles filled with medication items, with each receptacle corresponding to a particular time of a given day at which medication in the receptacle is to be taken, in any appropriate configuration (e.g., monthly dose pack, daily dose pack, etc)—the system 10 may be used with any such dose pack with arrays of receptacles representing different intake periods. Dose packs may thus have various medication items (i.e., tablets, capsules, sachets of powdered medication or the like) in a same receptacle. Indeed, although medication items may be provided in the form of tablets and capsules, the medication item may also be provided in the form of powder contained in a sachet (a.k.a., pouch or packet). In an embodiment, the dose packs may have receptacles which may be over-dimensioned for suitably receiving one or more of these sachets. For example, in addition to the array of receptacles of a dose pack representing intake periods of a day, an oversized receptacle may be provided in a day column or row to accommodate a powder sachet(s). It is noted that the sachets may be sealed and resealable. The use of medication item herein hence covers all medication types described above, unless stated otherwise.

The system 10 is used in conjunction with a table 11 which may or may not be part of the system 10, along with an assistance processor 12. The assistance processor 12 is used with an input such as a scanning device 13, user interface, imaging device, etc, and has an output 14, typically a computer screen or monitor along with peripherals such as a keyboard, mouse, printer, reader, etc, that will provide visual assistance to an operator who manually prepares the dose packs. The assistance processor 12 assists the operator in preparing medication dose packs based on dose pack prescription profiles and medication profiles. The dose pack prescription profiles and the medication profiles are illustrated as being stored in a database 15, which database may be part of the assistance processor 12, or accessible from pharmacy servers or from any other appropriate source. Moreover, the dose pack prescription profiles and the medication profiles may come from a same or from discrete databases. The dose pack prescription profiles are client-specific prescription files including posology data for medication types, etc. The medication profiles relate a first identifier (e.g., bar code, data matrix, etc) to a specific type of medication item, at a specific dosage, that may be disposed in one of many medication containers X accessible by the operator.

The table 11 is a support surface adapted to support dose packs in a predictable manner. Stated differently, the table 11 may have a virtual or physical matrix of positions in a plane of its support surface, with each position being a unique coordinate in a matrix. The table 11 is thus conceived to support multiple dose packs in such a way that each of the dose packs is positioned on the table 11 in a known or determinable position, whereby each of the receptacles of the dose packs on the table 11 has a unique location on the table 11 and a corresponding matrix address, which address is known or may be determined by the assistance processor 12. In FIG. 1, there is illustrated four different dose packs, labelled as dose packs 11A to 11D, positioned at four different positions A-D relative to the table 11. The system 10 of the present disclosure may operate with as little as two of the dose packs, more than two dose packs, or even more than the four dose packs illustrated in FIG. 1, provided the table 11 is sufficiently large. Although the expression table 11 is used, it should be pointed out that the table 11 may or may not necessarily be tangible. For instance, the table 11 may be virtual, with the assistance processor 12 and/or outlet 14 providing a light output to delimit the matrix surface of the table 11. Likewise, the medication dose packs lined up to be filled may be scanned (along with their position relative to one another) by the scanning device 13 so as to become the table 11.

The medication containers X typically identified by a first identifier such as a bar code, data matrix, or the like each contain a specific type of medication tablet or capsule (hereinafter, medication items) of specific dosage that will be used to prepare the various dose packs. The identification of the medication containers X may be obtained using the medication profiles stored in the database 15. In an embodiment where the medication item is provided in the form of powder contained in a sachet, it may be convenient to dispose and/or mark the first identifier directly on the sachet so that the operator can scan each one of the sachets using the scanning device 13. In an embodiment, the same first identifier may be marked on a medication container X and/or to a plurality of sachets disposed in the medication container X. In such a situation, the operator can scan the medication container X and/or scan the sachets each having their corresponding first identifier prior to filling the sachets in the appropriate receptacle of the dose packs, for instance.

The assistance processor 12 is any suitable processor unit capable of performing the calculations set forth herein below. Moreover, the assistance processor 12 has an operating system 21 to facilitate the interfacing of the operator with the output 14. Indeed, the assistance processor 12 will be used to visually guide an operator in preparing dose packs, whereby the output 14 is typically an interface that provides the information in a suitable visual manner to precisely guide the operator.

In order to start preparing the dose packs, the operating system 21 must know the position of the dose packs on the table 11, to associate a matrix address to each of the receptacles of each dose pack on the table 11. According to an embodiment, the dose packs may already be labelled with a second identifier corresponding to a dose pack job such as a periodic prescription associated with a given client. The scanning device 13 may be used to scan the second identifier (bar code, number, alpha-numerical code, etc.) on the dose packs, as well as their positions on the matrix of the table 11. The second identifier may alternatively be manually entered by an operator of the system 10, when a number is used.

In accordance with an embodiment, the system 10 may have access to hundreds of dose pack prescription profiles and medication profiles from the database 15. The assistance processor 12 will determine the identity of the dose pack jobs to be performed. This determination may be based on operator preferences, such as alphabetical order, room number (e.g., in a hospital), etc. The second identifier that may correspond to one of the dose pack jobs will be recognized by the assistance processor 12 throughout the preparation and verification steps as described hereinafter, whereby its medication inventory per receptacle will be known by the assistance processor 12. In an embodiment, the output 14 produces a label with the second identifier, which label may be added to an empty dose pack.

By identifying the second identifier of the dose packs, a dose pack prescription profile for each of the dose packs 11A to 11D may be obtained, which dose pack prescription profile contains medication items per intake time period, i.e., per receptacle of the dose pack. By using the scanning device 13 to obtain this information, the operation system 21 will know for instance that the dose pack 11A is located at position A on the table 11 and hence be able to provide an address on the matrix of table 11 to each of the medication items that will be used in filling the dose pack 11A in accordance with the dose pack prescription profiles and the medication profiles stored in the database 15. It is pointed out that this identifying operation may be performed manually when the input is provided in the form of a keyboard, mouse, and/or touchscreen of the output 14 to enter the information regarding the position and dose pack job (using the second identifier) of the dose packs on the table 11, as an alternative to the scanning device 13.

Using the data obtained with the second identifier and position of the dose packs 11A-11D, the dose pack medication localizer 22 then determines a position for each of the receptacles of the dose packs and performs an inventory of all medication items that must be used to fill all receptacles of all dose packs, with each of the medication items being given an address on the matrix of the table 11. The matrix address corresponds to a specific receptacle of a specific one of the dose packs 11A-11D, in accordance with the dose pack prescription profiles.

The medication grouper 23 will then use the inventory and address data from the dose pack medication localizer 22 to group the medication items by type. More specifically, in order to minimize the number of movements performed by the operator in manually filling the multiple dose packs, and therefore accelerate the completion of the dose-pack preparation job, the assistance processor 12 will guide the operator in filling all receptacles of all dose packs 11A to 11D that require a first type of medication item. As the filling of a receptacle with a medication item must be preceded by a verification of the identity of the medication item (e.g., by scanning or entering the first identifier associated with the medication container X), a random distribution of medication items, or a preparation of dose packs one at a time may lead to an excessive number of verification manipulations. Accordingly, the distribution of a first type of medication in multiple dose packs simultaneously will minimize the number of times that the medication containers X must be scanned (i.e. they must be scanned a single time if the medication container X has a sufficient amount of medication items).

A distribution matrix generator 24 is then used to prepare a sequence of manual filling for the operator. More specifically, the distribution matrix generator 24 will produce a visual output for the output 14 that consists of the identity of the medication item from a single one of the medication containers X, as well as matrix addresses of all receptacles of the multiple dose packs 11A-11D that must be filled with this medication item. For instance, the distribution matrix generator 24 may be a grid on a monitor of the output 14 visually representing the receptacles on the table 11 with a light indication pointing to each of the receptacles that must be filled (e.g., sequentially lit up as the receptacles are being filled by the specific medication item). The matrix table 11 itself may have as part of the output 14 some backlit surface to light up the bottom of the receptacles corresponding to identified addresses or a light projector projecting a light beam to identify what receptacles must be filled, as an alternative or supplemental means to perform this guiding function. As yet another alternative, the output 14 may be a printout comprising all necessary visual representation needed for assisting the manual filling of the dose packs 11A-11D on the table 11. The distribution matrix generator 24 also indicates how many medication items must be deposited in each receptacle if there is more than one medication item of same identity in a single receptacle.

Hence, the distribution matrix generator 24 provides a distribution sequence by which the filling of the dose packs will be optimized. Indeed, the distribution sequence may include steps associated with the sequential filling of each one of the medication items, combining multiple dose pack jobs. The distribution matrix generator 24 may also keep track of the filling jobs as a function of the medication profiles stored on the database 15. For example, by accessing the medication profiles stored on the database 15, the generator 24 may note, based on the tracking, that the inventory of a given medication item is insufficient to complete the filling jobs of the multiple dose packs 11A-11D. The generator 24 may thus keep track of the uncompleted jobs (i.e., an identification of the medication items and address therefor) to allow the operator to postpone the completion of a job to complete same later when the inventory issue is resolved.

A filling verifier 25 is used along with the distribution matrix generator 24 to verify that the right medication items are used in the filling jobs, in accordance with the prescription profiles. More specifically, the filling verifier 25 will receive data from the scanning device 13 and compare with that of the medication profiles stored on the database 15, as a response from the operator being prompted to scan a medication container X, and will authorize the distribution matrix generator 24 to provide its output only once the identity of the medication container X has been verified using the first identifier, for instance. Alternatively, the operator may randomly obtain the output from the distribution matrix generator 24 by scanning one of the medication containers X, as the filling verifier 24 will direct the distribution matrix generator 24 to provided addresses for the identified medication container X. Accordingly, the filling verifier 25 will ensure that the adequate medication container X is used prior to the distribution of its medication item. It may for instance be arranged that the output of the distribution matrix generator be available only once the filling verifier 25 confirms that the appropriate medication container 12 has been scanned.

Moreover, the filling verifier 25 may also verify that a proper identity label is given to each filled one of the dose packs, whereby the identity label may be used to identify and seal each of the filled dose pack. For instance, the identity label may also be used to identify the client, the operator and any other information deemed useful. In another embodiment, the identity label has a third identifier which can be scanned with the scanning device 13 in order to confirm that it is being associated with the right dose pack. In other words, the system can associate the second identifier of the filled dose pack with the third identifier of the identity label prior to sealing the identity label to the filled dose pack when the dose pack job is deemed done. The second and third identifiers may be the same. For instance, a sequence of scanning (1) the second identifier associated with a dose pack job, (2) the position of the dose pack and (3) the third identifier of the identity label (in any appropriate order), may be required to approve a dose pack before it is removed from the system 10.

The system 10 may have a safety module, such as a biometric reader or like ID verifier (PIN, IC card, etc) to authenticate the operator that wants to perform jobs. The output 14 may also produce labels or like data sheets that will contain all necessary information to identify the dose packs, such as patient identity, job operator identity.

In another embodiment, a post-filling verification step may be required prior to delivering the filled dose pack to the client. The post-filling verification step may be performed only by authorized personnel such as certified technicians and/or pharmacists. The post-filling verification step typically begins with a scan of the third identifier associated with a dose pack so that the system 10 can recognize which dose pack is to be verified with its corresponding visual validation grid. Then, the filling verifier 25 may cause the output 14 to display the visual validation grid, i.e. images of the medication items that should be in each one of the receptacles of the filled dose pack. Such a visual validation grid may involve an exploded view with actual pictures of each one of the medication items. Then, the filling verifier 25 may be configured to cause the output 14 to display the images of the medication items associated with each receptacles, one at a time, so that the authorized personnel can verify each receptacles sequentially. In another embodiment, the filling verifier 25 may be configured to display the images of the locations of receptacles having the same medication items so that the authorized personnel can verify efficiently each grouping one after the other. In still another embodiment, images of the location of the receptacles of a same grouping may blink so that the authorized personnel can easily identify which receptacles of the filled dose pack to verify. It is noted that the visual validation grid may provide indications to the authorized personnel to scan a first identifier located on a powdered-medication sachet for validating that the sachet is disposed in the right receptacle.

Figure 2:
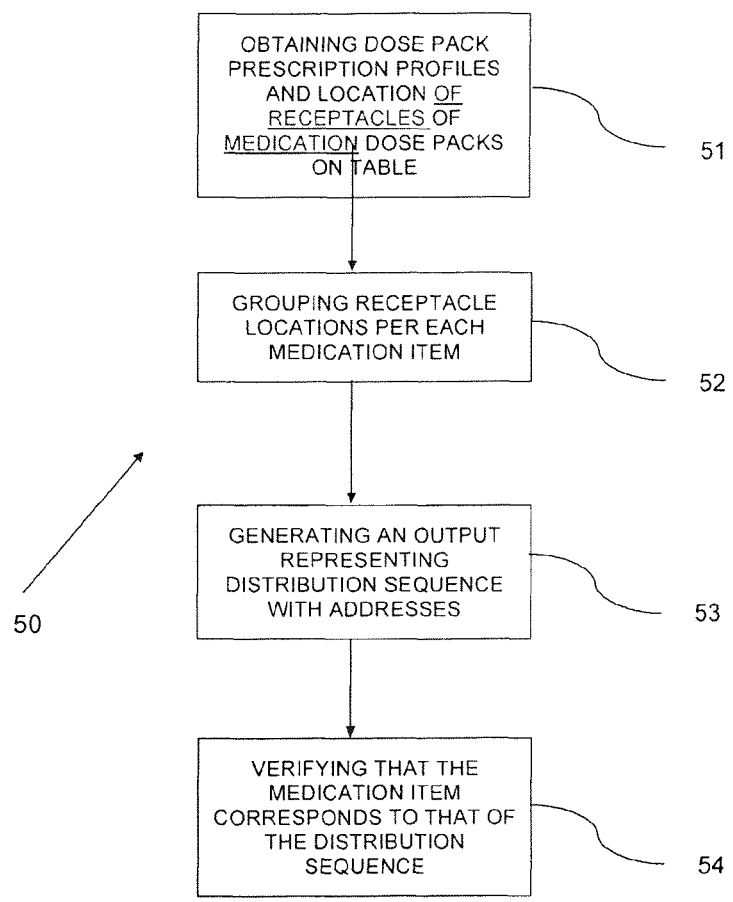
FIG. 2 is a flow chart of a method for assisting the preparation of medication dose packs in accordance with the present disclosure.

During the post-filling verification step, the dose pack may or may not be sealed with the identity label so that the filling verifier 25 may be adapted to display the visual validation grid in an orientation which can be read conveniently by the authorized personnel. For instance, when the dose pack is not sealed, a monitor of the output 14 may display a visual validation grid having a morning medication shown to the far right of the monitor and when the dose pack is sealed, the monitor may display the visual validation grid having the morning medication receptacle shown to the far left of the monitor. Now that the system 10 has been described, a method for assisting an operator in the preparation of client specific medication dose packs is described. The method is generally shown at 50 in FIG. 2, and may be implemented by the system 10 or any other adequate system. The method 50 is performed as a function of dose-pack preparation jobs to be done. The operator therefore has empty dose packs, each with a second identifier (or each given a dose pack job) corresponding to a dose pack prescription profile associated to a client.

According to 51, dose pack prescription profiles are obtained, as well as positions of dose packs on a distribution table, for a given number of dose pack jobs. This may be done by receiving manually entered or scanned data corresponding to a position of given empty dose packs on the table. By obtaining this information, a matrix address is determined for each receptacle of the multiple dose packs on the table, and this matrix address is matched with the identity of the medication item(s) that must be deposited in the receptacle.

According to 52, the matrix addresses of the receptacles are grouped for each of individual medication item obtained in the dose pack prescription profiles. For instance, a specific medication item will be given numerous matrix addresses, each corresponding to a receptacle. This grouping is not client-specific, but rather done jointly for all dose pack jobs on the table.

According to 53, an output representing a distribution sequence for the medication items is generated using the grouping of 52, which distribution sequence comprises the addresses corresponding to the various receptacle locations. The distribution sequence typically comprises a sequence of steps showing the positions of all dose packs to be filled up with a single type of medication item, to then switch to another type of medication item once the filling job is completed for the first type of medication item. The output may provide other information, such as incomplete dose pack jobs, unavailable medication items (e.g., no inventory), etc.

According to 54, a step of verification is performed to ensure that the medication item used to fill the dose packs corresponds to the medication item that has been identified in the distribution sequence. The verification may be done by obtaining scanning data of a medication container. This verification may be done before the distribution sequence data is fully provided. In some instances, alternative verification methods may be used.

While the above description refers to dose packs that are empty, it is pointed out that the system 10 and method 50 may be used to complete some jobs that were left incomplete. For instance, the system 10 and method 50 could be used with automated equipment, which automated equipment has limited medication storage capacity. Hence, the manual steps performed with the assistance of the system 10 and/or method 50 could be to finalize jobs of incomplete dose packs.

The invention claimed is:

1. A system for reducing an amount of time for filling of at least eight medication dose packs laid on a support surface, each said medication dose pack having at least 28 receptacles adapted to receive medication items based on dose pack prescription profiles of a plurality of clients, the receptacles of each said medication dose pack arranged in an array of rows and columns, the system comprising:
an assistance processor comprising:
a dose pack medication localizer for obtaining the dose pack prescription profiles for each said medication dose pack for all of the plurality of clients, and for determining a location of each receptacle of each said medication dose pack on the support surface, and for identifying medication items required in each said receptacle of each said dose packs using the dose pack prescription profiles;
a medication grouper for grouping, for each of the medication items of the dose pack prescription profiles of all of the at least eight medication dose packs and all of the plurality of clients, the locations of each said receptacle of each said dose packs on the support surface to be filled with at least a corresponding one of the medication items; and
a distribution matrix generator for generating a filling sequence for filling the dosepacks on the support surface using each one of said grouping, the filling sequence including at least an identification of all of said receptacles of all of said medication dose packs to be filled with a first type of medication item for all of the plurality of clients, sequentially before an identification of all said receptacles of all of said medication dose packs to be filled with a second type of medication item for all of the plurality of clients, wherein the filling sequence includes an identification of at least two receptacles of a first of the medication dose packs to be filled with the first type of medication item prior to a filling of a second of the medication dose packs with the first type of medication and wherein the filling sequence may include filling one of the at least two receptacles of the first of the medication dose packs with the second type of medication; and
an output for producing the filling sequence for assisting the filling of the dose packs with the medication items.

2. The system of claim 1, wherein the assistance processor is configured to receive position data for each said dose pack from an input for said determining the locations of the receptacles of the dose packs on the support surface.

3. The system of claim 1, wherein the dose pack medication localizer is configured to determine the locations of the receptacles of each dose pack based on positions of each dose pack on the support surface and on a standard configuration of the dose pack.

4. The system of claim 1, wherein the system includes a safety module for authenticating an operator operating the assistance processor.

5. The system of claim 1, wherein the output is adapted to provide the visual representation on the support surface, over said dose packs, and indicate which receptacles are to be filled for each one of said grouping.

6. The system of claim 1, wherein the assistance processor further comprises a filling verifier for verifying that the right medication item is used for the filling of the receptacles associated with each one of said grouping.

7. The system of claim 6, wherein the filling verifier is configured to cause the output to display a visual validation grid for verifying dose packs after filling in accordance with the filling sequence.

8. The system of claim 6, wherein at least one of verifying with the filing verifier and determining the location with the dose pack medication localizer includes scanning at least one identifier.

9. The system of claim 1, wherein the distribution matrix generator is configured to keep track of the filling of the medication dose packs based on an inventory of the medication items for each grouping.

10. The system of claim 9, wherein the distribution matrix generator is configured to identify the filling of one of the dose packs as incomplete based on said tracking.

11. The system of claim 1, wherein the identification in the filling sequence of all said receptacles of all of said medication dose packs to be filled with a first type of medication item includes an indication that at least two of the first type of the medication items is required in any one of the receptacles of the medication dose cards.

12. A method for reducing an amount of time required for filling of at least eight medication dose packs associated with a plurality of clients, the at least eight medication dose packs laid on a support surface, each said medication dose pack having at least 28 receptacles adapted to receive medication items, the receptacles of each said medication dose pack arranged in an array of rows and columns, the method comprising:
obtaining dose pack prescription profiles for all of the plurality of clients associated with the at least eight medication dose packs;
determining locations of the receptacles of the medication dose packs on the support surface;
grouping, for each one of a plurality of medication items of the dose pack prescription profiles of all of the at least eight medication dose packs and all of the plurality of clients, the locations of each receptacle of each said medication dose packs to be filled with at least a corresponding one of the plurality of medication items; and
generating and outputting a filling sequence having steps each indicating which receptacles of the medication dose packs to fill in accordance with one of said grouping and to be performed sequentially for filling the medication dose packs, the filling sequence including at least an identification of all said receptacles of all of said medication dose packs to be filled with a first type of medication item for all of the plurality of clients, sequentially before an identification of all said receptacles of all of said medication dose packs to be filled with a second type of medication item for all of the plurality of clients, wherein the filling sequence includes an identification of at least two receptacles of a first of the medication dose packs to be filled with the first type of medication item prior to a filling of a second of the medication dose packs with the first type of medication, and wherein the filling sequence may include filling one of the at least two receptacles of the first of the medication dose packs with the second type of medication.

13. The method of claim 12, further comprising, for each one of the steps of the filling sequence, verifying that the medication item used by the operator corresponds to that of the step of the filling sequence.

14. The method of claim 13, wherein at least one of verifying and determining includes scanning at least one identifier.

15. The method of claim 13, wherein said verifying includes tracking the filling of the medication dose packs based on an inventory of the medication items for each grouping.

16. The method of claim 15, wherein said tracking includes identifying one of the medication dose packs as incomplete based on said tracking.

17. The method of claim 15, further comprising outputting an identity label for the filled one(s) of the medication dose packs based on said tracking.

18. The method of claim 12, further comprising sequentially outputting a visual representation of the steps of the filling sequence for assisting the manual filling of the medication dose packs with the medication items.

19. The method of claim 18, further comprising verifying that the receptacles associated with one of the steps are filled with the corresponding medication item prior to outputting a subsequent step of the filling sequence.

20. The method of claim 18, wherein said outputting includes providing the visual representation on the support surface, over said medication dose packs, and indicating which receptacles are to be filled for each one of said grouping.

21. The method of claim 12, wherein said determining includes receiving data from an input operable by an operator.

22. The method of claim 12, further comprising outputting a visual validation grid for verifying the dose packs after filling in accordance with the filling sequence.

* * * * *